(12) United States Patent
Von Schuckmann

(10) Patent No.: US 7,827,984 B2
(45) Date of Patent: Nov. 9, 2010

(54) INHALER DEVICE

(76) Inventor: Alfred Von Schuckmann, Winnekendonker Str. 52, D-47627 Kevelaer (DE)

(*) Notice: Subject to any disclaimer, the term of this patent is extended or adjusted under 35 U.S.C. 154(b) by 786 days.

(21) Appl. No.: 11/747,051

(22) Filed: May 10, 2007

(65) Prior Publication Data

US 2007/0240708 A1    Oct. 18, 2007

Related U.S. Application Data

(63) Continuation of application No. PCT/EP2005/054138, filed on Aug. 23, 2005.

(30) Foreign Application Priority Data

Nov. 10, 2004   (DE) ..................... 10 2004 054 179
Jul. 18, 2005    (DE) ..................... 10 2005 033 398

(51) Int. Cl.
*A61M 11/00* (2006.01)

(52) U.S. Cl. ............... 128/200.23; 128/200.14; 128/203.12; 128/203.15; 128/205.23

(58) Field of Classification Search ........... 128/200.24, 128/203.12, 203.15, 203.23, 200.14–200.23; 222/32, 36, 38; 116/307, 311, 312, 317, 116/318

See application file for complete search history.

(56) References Cited

U.S. PATENT DOCUMENTS

| | | | |
|---|---|---|---|
| 5,228,586 A | 7/1993 | Fuchs | |
| 5,971,140 A | 10/1999 | Frutin | |
| 6,283,365 B1 * | 9/2001 | Bason | 235/116 |
| 6,431,168 B1 | 8/2002 | Rand et al. | |
| 6,446,627 B1 | 9/2002 | Bowman et al. | |
| 7,464,708 B2 * | 12/2008 | Marx | 128/205.23 |
| 2004/0144798 A1 | 7/2004 | Ouyang et al. | |
| 2004/0149772 A1 * | 8/2004 | Ouyang | 222/36 |
| 2004/0211420 A1 | 10/2004 | Minshull et al. | |

FOREIGN PATENT DOCUMENTS

| | | |
|---|---|---|
| EP | 0 480 488 A1 | 7/1991 |
| EP | 1 065 477 A2 | 3/2000 |
| WO | WO 01/28887 A1 | 4/2001 |
| WO | WO 2004/071563 A1 | 8/2004 |

OTHER PUBLICATIONS

International Search Report, Mar. 7, 2006, 8 pages.

* cited by examiner

*Primary Examiner*—Kevin C. Sirmons
*Assistant Examiner*—Valerie Skorupa
(74) *Attorney, Agent, or Firm*—St. Onge Steward Johnston & Reens LLC

(57) ABSTRACT

The invention relates to a hand-held device for apportioned delivery of sprayable substances, in particular inhaler medicaments the device, having a cartridge which is displaceable by pressing in a housing into the open position for delivery, and an indexing mechanism which is moved along by the cartridge during the opening stroke of the cartridge for registering and displaying delivery actuations which have been carried out. The feeding mechanism, which indexing mechanism is disposed in a housing centrally below the opening-side end wall of the cartridge, overlappinqly with respect to the valve tube of the cartridge. In order to configure a hand-held device of the type in question in a spatially advantageous manner with a simplified construction and such that it is more reliable in terms of handling, it is proposed to displace plate-shaped housing as a whole with the cartridge, except for a step-by-step indexing finger star disposed therein.

7 Claims, 6 Drawing Sheets

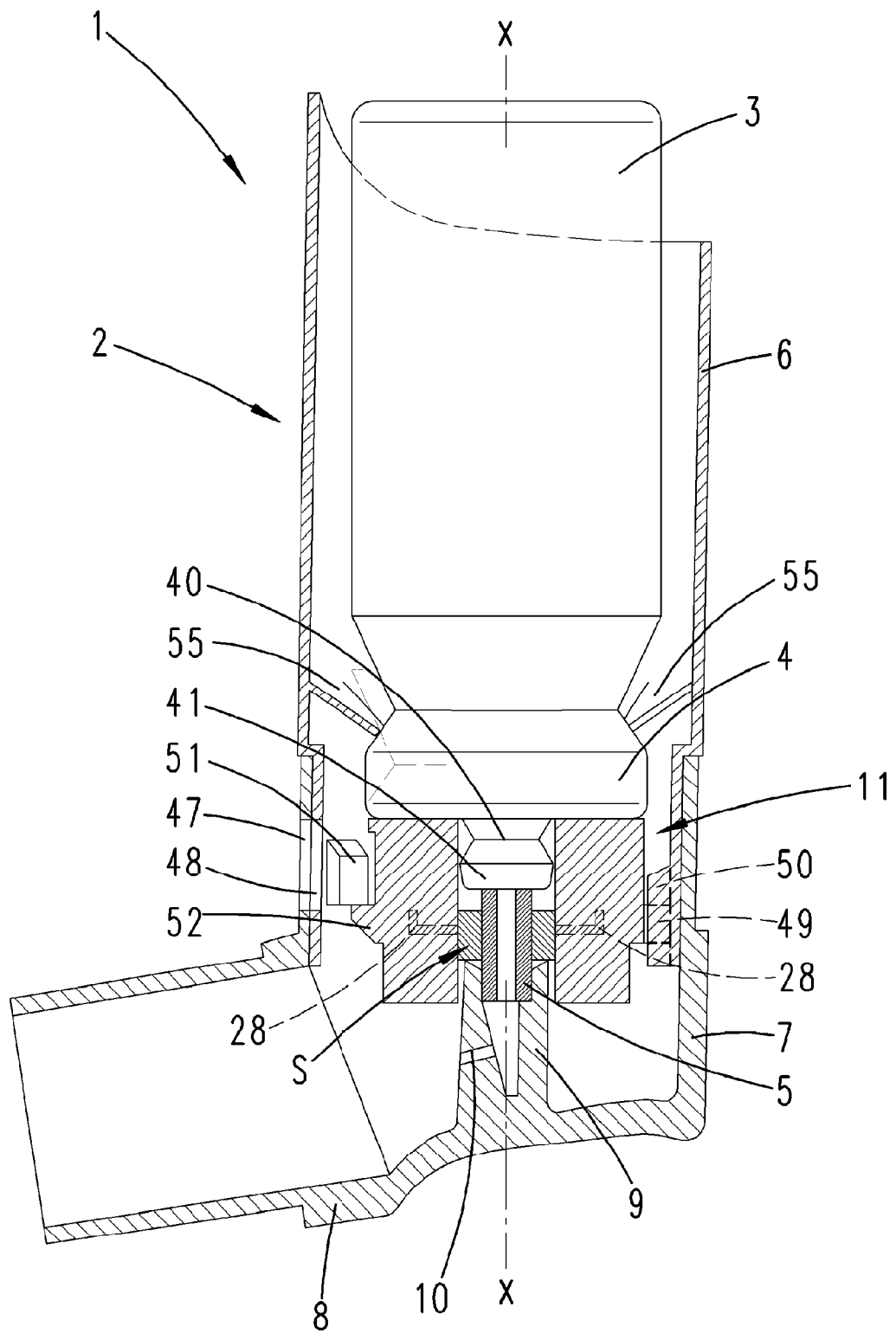

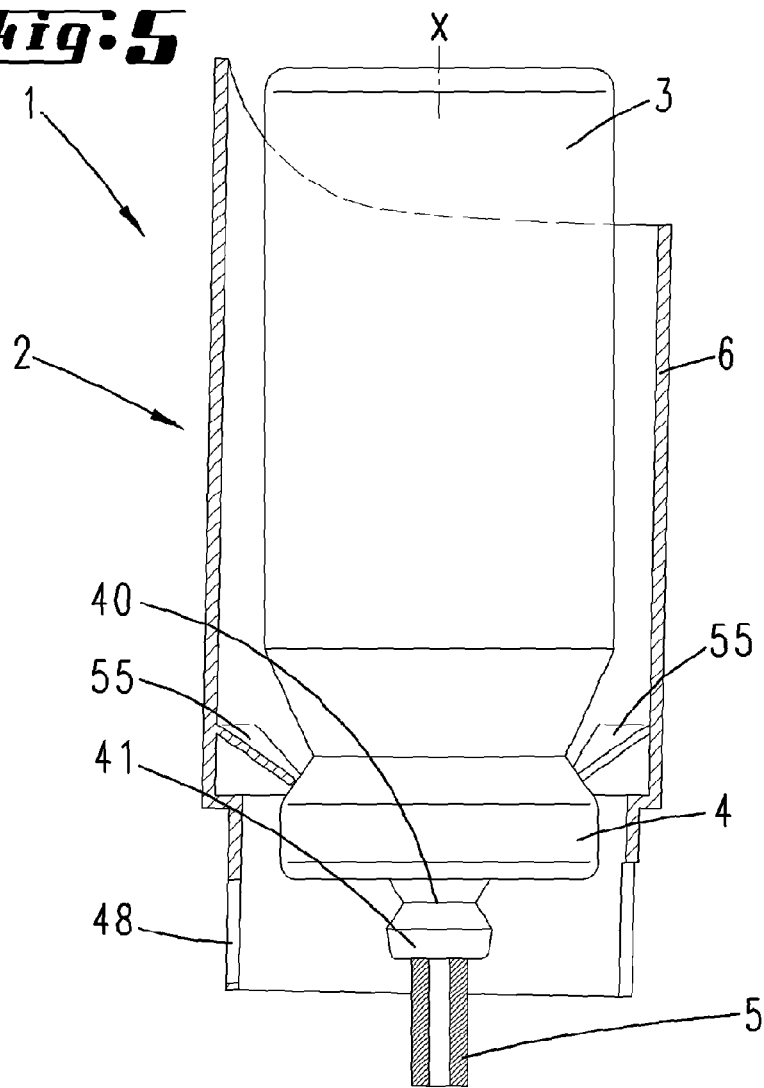
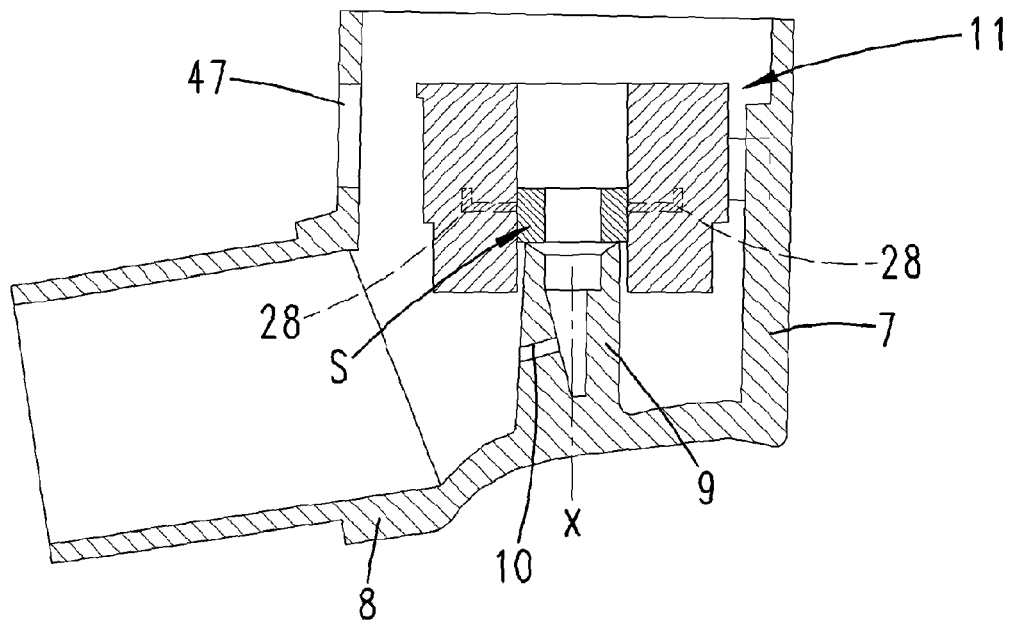
Fig. 5

INHALER DEVICE

CROSS-REFERENCE TO RELATED APPLICATIONS

The present application is a continuation of pending International patent application PCT/EP2005/054138 filed on Aug. 23, 2005 which designates the United States and claims priority from German patent applications Nos. 10 2004 054 179.5 filed on Nov. 10, 2004 and 10 2005 033 398.2 filed on Jul. 18, 2005. All prior applications are herein incorporated by reference.

FIELD OF THE INVENTION

The invention relates to a hand-held device for apportioned delivery of sprayable substances, in particular inhaler medicaments, according to the preamble of the main claim.

BACKGROUND OF THE INVENTION

Hand-held devices of the type in question are known (US 2004/0149772). They are used in particular in medicinal aerosol therapy for the treatment of respiratory diseases. There, a step-by-step indexing mechanism is provided, the construction of which is disadvantageous with regard to the space required and possibilities for cleaning.

The invention is therefore based on the problem of configuring a hand-held device of the type in question in a spatially advantageous manner with a simplified construction and such that it is more reliable in terms of handling.

SUMMARY OF THE INVENTION

This problem is solved first and foremost by the subject matter of Claim 1, this being based on a step-by-step indexing mechanism which is disposed in a plate-shaped housing and has indexing members such that during movement of the cartridge, the entire housing and the step-by-step indexing mechanism is moved along with it, except however for a step-by-step indexing finger star. As a result of such a configuration, a hand-held device of the type in question is realised, which, because of the construction selected, is formed advantageously both with regard to the space required and with regard to the possibilities for cleaning and, in addition, also with regard to the capability for being handled. A mechanically operating step-by-step indexing mechanism is realised which, owing to the selected location of the various indexing members, in particular the step-by-step indexing finger star, has an advantageous, space-saving constructional form, for which the free space which is present below the cartridge in the hand-held device housing can be used here. If the step-by-step indexing mechanism is to be removed (with or without the cartridge) for cleaning purposes, the risk of a change in the position of the counting mechanism is practically eliminated, because the step-by-step indexing finger star is accessible practically only with a handling tool, and even that is not possible in the case of a suspended cartridge.

The subject matter of the rest of the claims is explained hereinbelow in relation to the subject matter of Claim 1.

It is thus furthermore provided that the step-by-step indexing mechanism has a graduated ring which is rotated step-by-step by a toothed ring, which ring revolves concentrically with the valve tube and is driven by the opening stroke of the cartridge, via a planet-wheel gear mechanism. The rotational movement of the graduated ring is derived from the displacement of the cartridge by the step-by-step indexing mechanism, the step-by-step indexing finger star of which operates on a track around the valve tube of the cartridge. The indexing finger star is part of the integrally constructed step-by-step indexing mechanism and, in the operational position of the hand-held device, is supported in the region of the housing-side valve-tube receiving portion which at the same time forms the counter bearing for the valve tube with respect to the valve opening. In the event of possible removal of the step-by-step indexing mechanism from the housing, the absence then of the supporting portion for the indexing finger means that an inadvertent, cartridge-independent actuation of the step-by-step indexing mechanism is not possible. It is furthermore provided that the planet wheel is mounted in a hole in the graduated ring and the associated sun wheel is seated on a disk having teeth on the lower side. This disk is in engagement with the indexing finger. A latching finger also engages in the toothing, in order to secure the rotational position of the disk that has been reached in each case. Sun wheel and toothed disk are preferably formed in one piece, with a coaxial alignment. It is furthermore preferred that the graduated-ring graduation, which is disposed on the outer circumferential surface of the graduated ring and runs in front of a viewing window of the housing, corresponds in each case to a plurality of individual rotary steps of the planet wheel. In this regard, it has furthermore proven advantageous that, with regard to the step-down ratio, an individual rotary step of the planet wheel takes place after a plurality of individual rotary steps of the sun wheel have taken place. The planet wheel is furthermore in engagement radially on the outside with a toothed ring. The latter has at least one slot extending from the lower peripheral edge in a direction obliquely upwards, for entry of the step-by-step indexing finger in order thereby to predetermine the indexing direction of the finger for the step-by-step continued rotation of the disk on the sun-wheel side. The step-by-step indexing finger or fingers are directed obliquely upwards extending from the hub, the step-by-step indexing fingers furthermore moving in the direction of a plane perpendicular to the longitudinal axis during the delivery stroke of the cartridge.

After release of the cartridge, the latter hurries back into its basic position on account of the integrated valve spring, causing the step-by-step indexing-mechanism housing to lag behind because it is now not being acted upon. This is achieved by the prestressed step-by-step indexing fingers which automatically take up their original, obliquely upwardly directed position again and in the process press the indexing members and the step-by-step indexing-mechanism housing into their original position. Accordingly, the step-by-step indexing mechanism is decoupled from the cartridge with regard to being displaced back into a basic position. The step-by-step indexing mechanism housing, which is configured as a flat plate, has a central hole for the passage of the valve tube, which hole widens at the cartridge end for the entry of a collar which protrudes on the opening side of the cartridge and behind the region of which a resilient latching between step-by-step indexing-mechanism housing and cartridge takes place. The resilient latching between step-by-step indexing-mechanism housing and cartridge may be selected in such a manner that it cannot be undone without a tool. The axial length of the entire step-by-step indexing-mechanism housing is furthermore preferably matched to the length of extent of the valve tube; accordingly, the latter furthermore remains enclosed in a protected position by the step-by-step indexing-mechanism housing in the position in which it is removed from the hand-held device housing. As an alternative, the step-by-step indexing-mechanism housing, which is configured as a flat plate, may be latched in the hand-held device housing in such a manner that it can still be displaced inwards by the opening stroke. Thus, for example during a first equipping of the hand-held device, the step-by-step indexing-mechanism housing can be pushed together with the cartridge into the hand-held device housing, whereupon the step-by-step indexing-mechanism housing finally engages behind a catch provided in the housing. In a development of the subject matter of the invention, a double latching of the step-by-step indexing-mechanism housing, which is configured as a flat plate, is provided in such a manner that, in addition to the latching on the collar of the cartridge, a second stronger latching takes place in the hand-held device housing. Before using for the first time, it is frequently necessary first to equip the hand-held device housing with the cartridge. In order to save the user a further working step, namely the equipping of the hand-held device with the step-by-step indexing mechanism, the latter may already be latched to the cartridge. If the cartridge is pulled out of the hand-held device housing after this for cleaning purposes, the latching between step-by-step indexing-mechanism housing and cartridge collar is undone, the step-by-step indexing mechanism accordingly remaining in the hand-held device housing. In this regard, it has also proven advantageous if the stronger latching in the hand-held-device housing can itself be released after removal of the cartridge from the hand-held device housing. In an alternative configuration, it can be provided that the cartridge is blocked against being pulled off by means of retaining fingers which are formed pointing obliquely downwards in the hand-held device housing. Such a solution is advantageous in particular if no connection, in particular latching connection, is provided between the step-by-step indexing-mechanism housing and the cartridge.

BRIEF DESCRIPTION OF THE DRAWINGS

The invention is explained in more detail below with reference to the accompanying drawing which merely illustrates various exemplary embodiments. In the drawing:

FIG. 4a shows a third embodiment in a sectional illustration according to FIG. 4, in which the cartridge is blocked in the hand-held device housing against being pulled off;

FIG. 5 shows, in an illustration of a longitudinal section, the hand-held device in a further embodiment, after separation of an upper housing part from a mouthpiece.

DETAILED DESCRIPTION OF THE INVENTION

Figure 3:
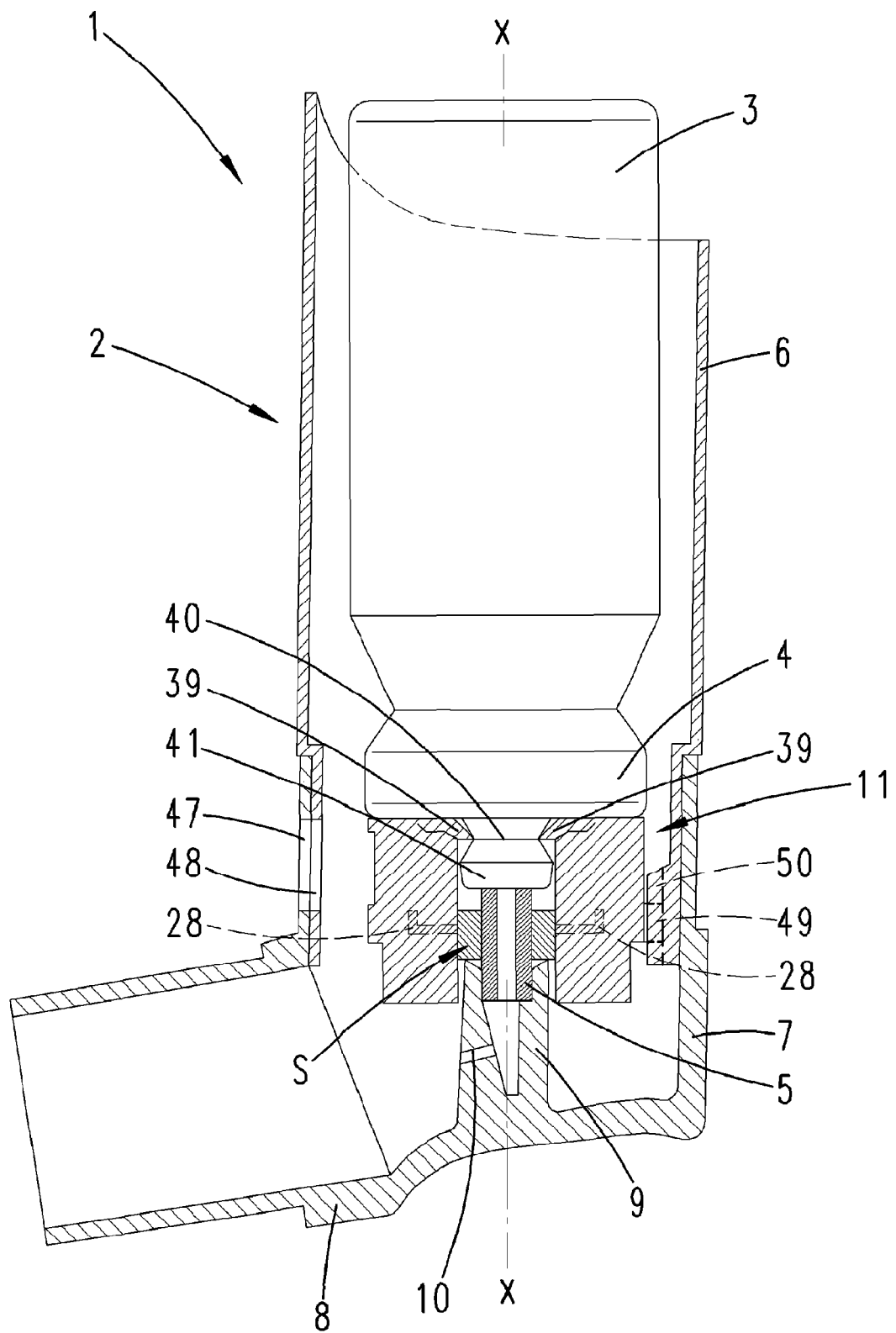
FIG. 3 shows, in an illustration of a longitudinal section, the hand-held device in a first embodiment, with a step-by-step indexing mechanism (illustrated diagrammatically) latched to a cartridge.

The hand-held device 1 shown in FIG. 3 in a diagrammatic sectional illustration is used for apportioned delivery of sprayable substances, in particular of inhaler medicaments.

For this purpose, the hand-held device 1 has in first instance a hand-held device housing 2 into which a cartridge 3 containing the sprayable substance can be inserted. This cartridge 3 is axially displaceable in the housing 2.

In conventional manner, the cartridge head 4 has a central valve tube 5 extending coaxially with the cartridge 3. A delivery of medicament is achieved via the said valve tube by an axial relative movement between cartridge 3 and housing 2.

The housing 2 is divided into two and substantially comprises two ring parts 6 and 7 which are disposed one above the other and of which the upper ring part 6 is formed in the manner of a shank and the lower ring part 7 has a mouthpiece 8 oriented approximately transversely with respect to the extent of the shank. The said mouthpiece can be closed by a covering cap (not illustrated).

The valve tube 5 of the cartridge 3 is supported in an associated tubular supporting portion 9 within the lower ring part 7, with axial movability of the cartridge 3 within the shank-like ring part 6 surrounding the cartridge 3.

The supporting portion 9, which accommodates the valve tube 5 of the cartridge 3 in a clamping manner and is formed within the lower housing ring part 7, is provided with a flow duct 10, which is reduced in diameter compared with a portion accommodating the end of the valve tube and is connected in terms of flow to the valve tube 5, that end of the flow duct 10 which faces away from the valve tube 5 pointing in the direction of the mouthpiece 8.

In the exemplary embodiment illustrated, the two ring parts 6 and 7 are connected to each other insertably. As an alternative, the two parts may also be connected to each other via a thread, for example via a coarse thread with a high pitch.

The positioning of the cartridge 3 in the housing 2 is selected in such a manner that the cartridge head 4 is placed in the housing 2 approximately level with the connecting region between ring part 6 and ring part 7.

Centrally below the opening-side end wall of the cartridge 3, a step-by-step indexing mechanism 11 is disposed in overlap with the valve tube 5 of the cartridge. This step-by-step indexing mechanism serves for registering and displaying the delivery actuations carried out, this taking place as a function of the opening strokes of the cartridge 3 that have been carried out.

Figure 1:
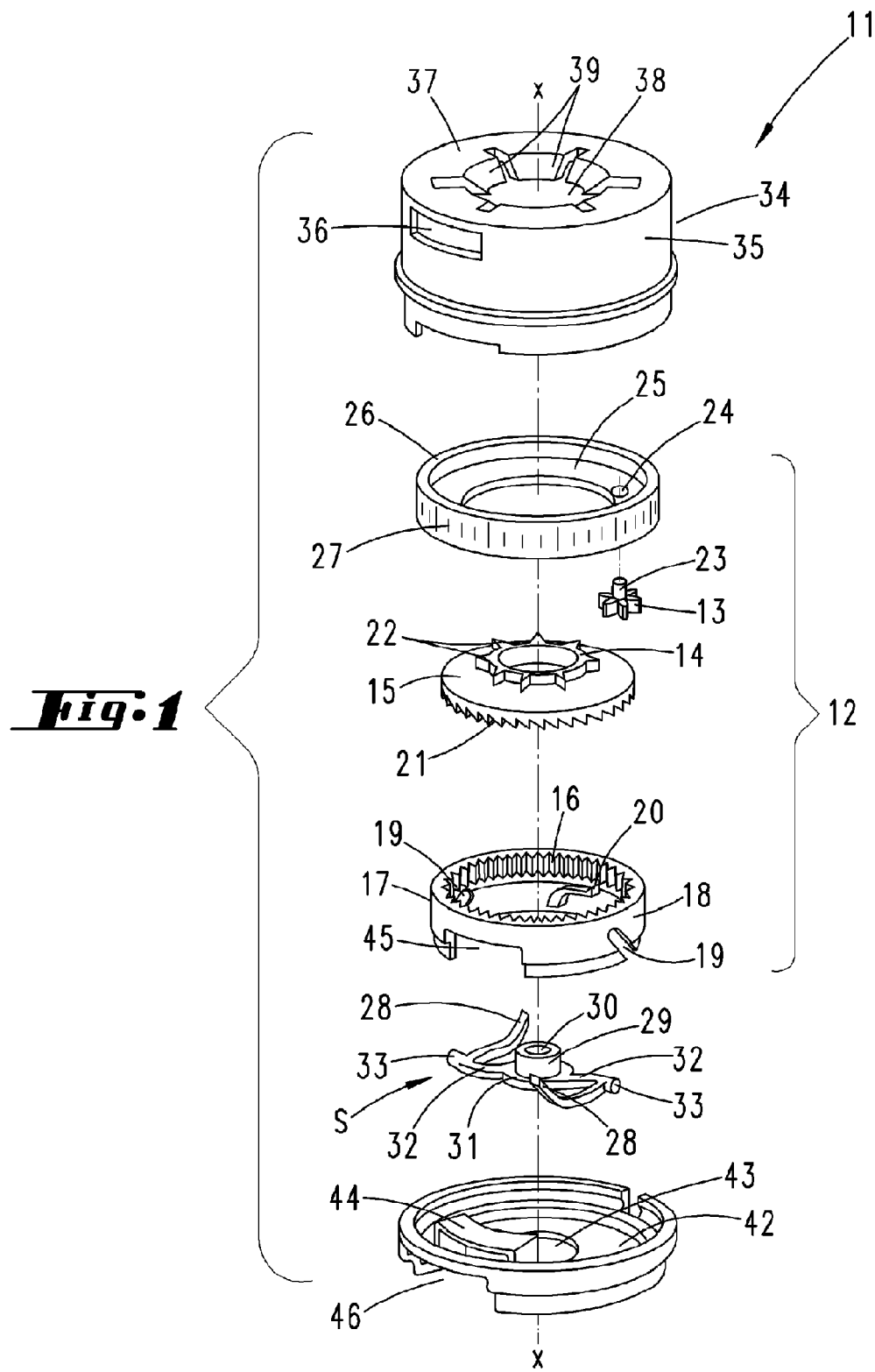
FIG. 1 shows, in perspective exploded illustration, the step-by-step indexing mechanism for the hand-held device according to the invention.

The step-by-step indexing mechanism 11 is shown in FIG. 1 in a perspective exploded illustration. The central part of the step-by-step indexing mechanism 11 is a planet-wheel gear mechanism 12, comprising a planet wheel 13, a sun wheel 14, which is seated on a disk 15 having teeth on the lower side, and a toothed ring 16 which interacts with the planet wheel 13. The said toothed ring is formed on the inside wall of a ring 17 which is mounted non-rotatably and is in the form of a portion of a tube. The circumferential wall 18 of the ring 17 is passed through, in diametrically opposite regions, by slots 19 which extend obliquely upwardly directed in the indexing direction and end downwardly open towards the ring edge which faces away from the toothed ring 16.

The toothed ring 16 extends in the axial direction approximately over half of the height of the ring 17, the circumferential wall 18 of which, which is stepped towards the ring end edge facing away from the toothed ring 16, being formed such that it tapers radially.

Below the toothed ring 16, a latching finger 20 is integrally formed on the inside of the circumferential wall 18 of the ring 17. With regard to a plan view of the ring, this latching finger is offset radially inwards with respect to the toothed ring 16; it correspondingly engages in a circular space drawn in radially inwards from the toothed ring 16. Furthermore, the location of the latching finger 20, which is formed elastically approximately in the vertical direction, is selected in such a manner that it engages approximately in a horizontal plane defined by the lower peripheral edges of the toothed ring 16.

The diameter of the disk 15 carrying the sun wheel 14 is selected to be slightly smaller than the inside diameter of the ring 17 in the region of the toothed ring 16. Sun wheel 14 and disk 15 are preferably formed in one piece, from the same material.

On the lower side of the disk 15, a circumferential serration 21 is provided around the edge, in which serration the latching finger 20 of the ring 17 engages.

The sun wheel 14 has a coarse toothing. Thus in the exemplary embodiment illustrated, eight sun-wheel teeth 22 are distributed uniformly over the periphery of the sun wheel 14. During the course of the rotation of the sun wheel, these teeth 22 interact with the planet wheel 13, which is disposed in the same plane between the sun wheel 14 and the toothed ring 16 of the ring 17.

The planet wheel 13 has a spindle 23 which protrudes upwards on one side, i.e. protrudes away from the disk 15 of the sun wheel 14. This spindle is held rotatably in a hole 24 in the region of a collar 25, which is directed radially inwards in the manner of a disk, of a graduated ring 26. The graduated ring 26 is provided on its outer peripheral wall with a circumferential graduation 27, the graduation corresponding in each case to a plurality of individual rotary steps of the planet wheel 13 driving the graduated ring 26 onwards.

The step-by-step displacement of the sun wheel 14 or of the disk 15 in one piece therewith takes place via step-by-step indexing fingers 28 formed in a manner such that they are deflectable resiliently, approximately vertically. These step-by-step indexing fingers 28 engage on the lower side in the serration 21 of the disk 15.

The step-by-step indexing fingers 28 are disposed diametrically opposite one another with regard to the main axis x of the step-by-step indexing mechanism 11 as a whole. For this purpose, in first instance a cylindrical central body in the form of a hub 29 is provided with a central, axial through hole 30. The diameter thereof is slightly larger than the outside diameter of the valve tube 5 of the cartridge, which is to pass through this through hole 30.

On the bottom side, the hub 29 merges into a radially widened collar 31. Integrally formed on the latter are guide portions 32 which protrude diametrically opposite one another in the radial direction and, in each case in the region of their free ends, form a guide pin 33 which is located in the associated slot 19 of the ring 17.

The step-by-step indexing fingers 28 are rooted in each case with a horizontal portion on the guide portions 32 with the guide pins 33 which protrude radially on the outside beyond the horizontal portion being left unaffected. The step-by-step indexing fingers 28 protruding from the horizontal portions extend in a direction obliquely upwards, for example enclosing an angle of 45 degrees with respect to the horizontal, matched to the slope of the slots 19 in the ring 17. The step-by-step indexing-finger star formed in this manner bears the reference symbol S.

The step-by-step indexing-finger star S, the ring 17 having the inner toothed ring 16, the disk 15 which is in one piece with the sun wheel 14 and the graduated ring 26 are aligned concentrically with one another on the axis x, with the height of the ring 17 being selected in such a manner that both the step-by-step indexing-finger star S and the sun wheel 14 together with disk 15 are accommodated therein.

The entire planet gear mechanism 12 and the step-by-step indexing-finger star S and the graduated ring 26 are accommodated in a cup-like step-by-step indexing-mechanism housing 34 with an outside diameter which is matched to the outside diameter of the cartridge 3.

The housing 34 has a circumferential wall 35. The latter has a viewing window 36 through which the graduation 27 of the graduated ring 26 can be seen.

Figure 2:
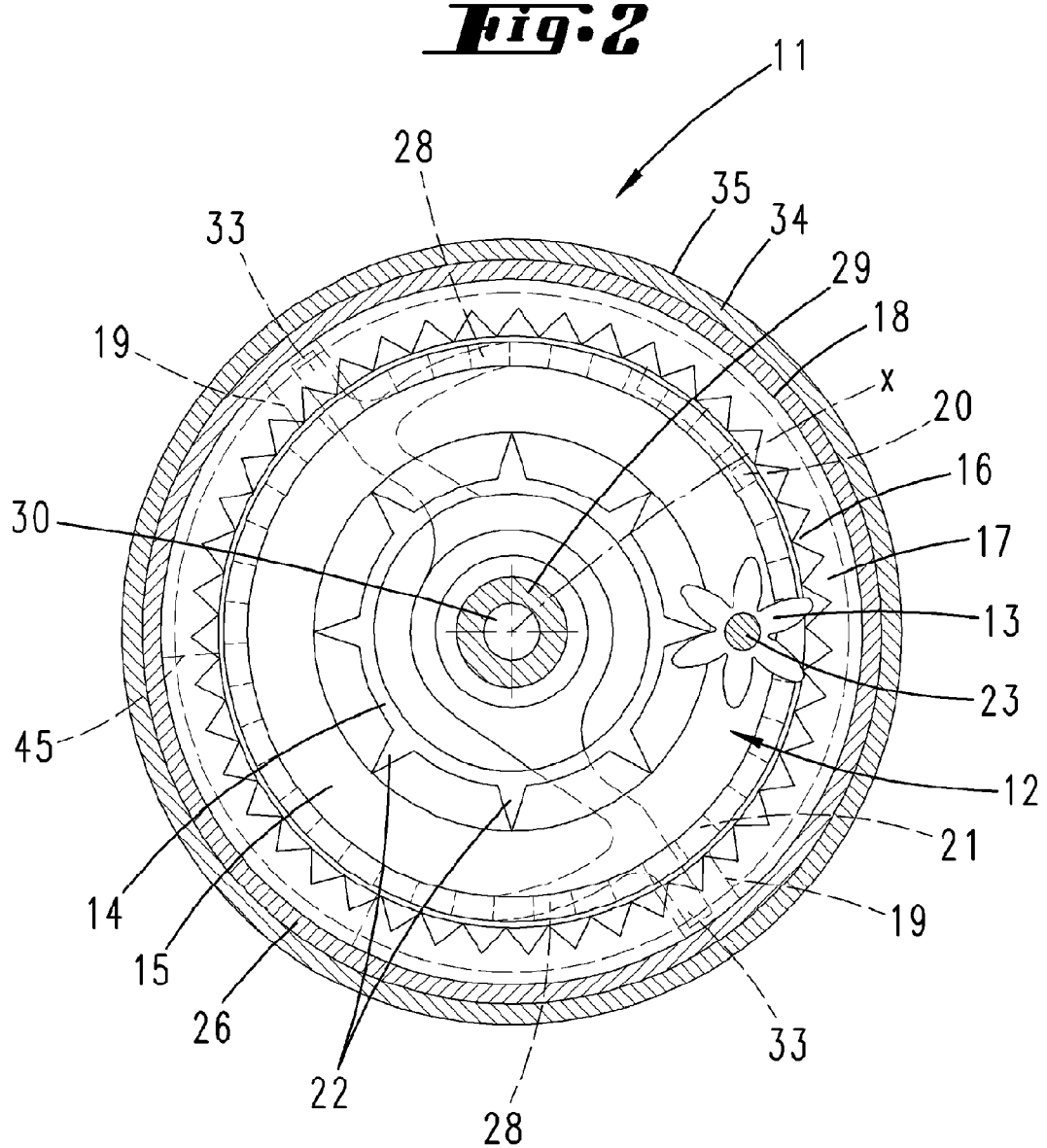
FIG. 2 shows a cross section through the step-by-step indexing mechanism.

The top of the housing 37 has a central break-through 38 which, in the embodiment shown in FIGS. 1 to 3, is surrounded by latching spring tongues, which taper conically towards the interior of the housing, in the embodiment 39 shown in FIGS. 1 to 3. The diameter of the break-through is matched to a diameter of a waist section 40 of a collar 41 which protrudes centrally above the opening-side end wall of the cartridge 3 and from which the valve tube 5 emerges.

The housing base 42 is formed by a separate part. This is connected to the housing 34, for example is welded to it or mounted on it via a press fit, with the previously described individual parts of the step-by-step indexing mechanism being accommodated.

The plate-like housing base 42 has a central hole for the passage of the valve tube 5. Also formed on the housing base 42 is a latching element 44 which, for securing the ring 17 in an oriented position, engages in a window-like recess 45 correspondingly formed in the circumferential wall 18 of the said ring.

In the same angular region in which the latching element 44 is disposed on the base, the outer circumferential wall of the housing base 42 has a clearance cut 46. In the installation state, the latter is associated with the region of the starting cross section of the flow duct 10 in the lower ring-part housing 7.

Figure 4:
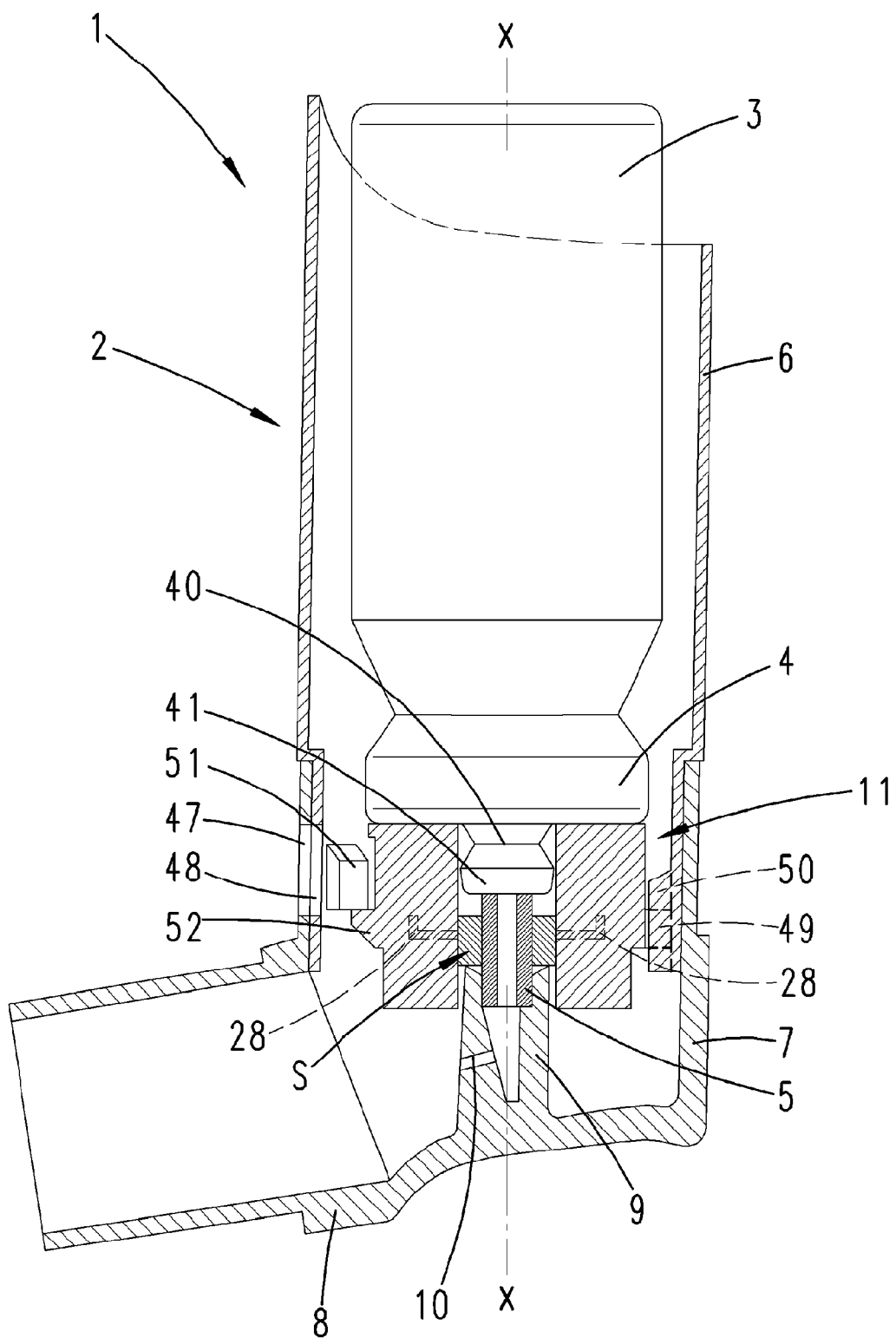
FIG. 4 shows a sectional illustration corresponding to FIG. 3, but relating to a second embodiment, in which the step-by-step indexing mechanism (illustrated diagrammatically) is latched to the housing.

The functioning of the step-by-step indexing mechanism 11 irrespective of the basic configuration still to be described with reference to FIGS. 3 and 4 is as follows:

The indexing members (step-by-step indexing-finger star S, ring 17, disk 15, planet wheel 13 and graduated ring 26) and the housing 34 with the housing base 42 are disposed on axes which extend in the longitudinal direction of the cartridge 3. Thus, with the exception of the planet wheel 13, all other components of the step-by-step indexing mechanism 11 are positioned on the longitudinal axis x-x of the cartridge.

The step-by-step indexing mechanism 11 is disposed within the housing 2 in the shadow of the cartridge 3 and correspondingly concentrically with the valve tube 5, to be precise in the construction space left between cartridge head 4 and supporting portion 9 of the housing 2. The step-by-step indexing mechanism 11 is supported with the hub 29 of the step-by-step indexing-finger star S, which hub is mounted centrally in the indexing-mechanism housing 34, on the end surface of the supporting portion 9 of the inhaler housing 2. The central axis x of the step-by-step indexing mechanism 11 is assumed by the axis of the body of the cartridge 3. The valve tube 5 passing through the hub 29 provides an additional means for centering the entire step-by-step indexing-mechanism unit.

When an actuating stroke of the cartridge 3 is carried out together with an associated vertical displacement of the same in the direction of the supporting portion 9, the indexing-mechanism housing 34 is carried along via the cartridge head 4, with displacement of the housing 34, the planet-wheel gear mechanism 12 and the graduated ring 26 relative to the step-by-step indexing-finger star S, which receives support on the supporting portion 9. As a result, the step-by-step indexing fingers 28, which are becoming stressed, with further assistance by the step-by-step indexing-finger star S sliding on in a rotating manner in the slots 19 in the circumferential wall of the ring 17, effect a step-by-step rotary advance of the serrated disk 15. In association with this, the sun wheel 14 rotates by the same angular amount. The step-by-step indexing fingers 28 move in this case out of the oblique orientation in the direction of a plane oriented perpendicularly with respect to the longitudinal axis x-x.

Owing to the fact that the sun wheel 14 only has eight teeth distributed uniformly over the circumference, not every step-type rotational movement of the sun wheel 14 leads inevitably to a rotational movement of the planet wheel 13. On the contrary, the rotation of the planet wheel 13 about its axis and an associated rotational displacement of the graduated ring 26 are carried out only after a plurality of individual rotational steps of the sun wheel 14.

According to the illustration in FIG. 3, the entire step-by-step indexing mechanism 11 can be fixed in a latching manner on the collar 41, which protrudes on the cartridge-head side, by means of the housing 34. In association with the housing-side viewing window 36, the associated portions of the housing ring parts 6 and 7 likewise have viewing windows 47, 48 which, owing to the position selected, facing the mouthpiece 8 of the housing 2, are located in the field of view of the user operating the hand-held device 1. In order to insert the step-by-step indexing mechanism 11 in an oriented position, it is provided with a guide blade 49 which protrudes radially from the housing 34 and engages in a vertical groove (not illustrated specifically) in the interior of the housing 2, permitting the displacement travel during actuation of the stroke.

The latching between step-by-step indexing mechanism 11 and cartridge 3 in the region of the collar 41 on the cartridge-head side is selected in such a manner that, if the cartridge 3 is removed from the housing 2, the step-by-step indexing mechanism 11 is pulled out at the same time while remaining on the cartridge 3.

Alternatively, there is also the possibility, as illustrated diagrammatically in FIG. 4, for the step-by-step indexing mechanism 11 to be latched to the housing 2. For this purpose, the step-by-step indexing mechanism 11, in the course of a first fitting, moves over one or more radially inwardly protruding latching projections 51 of the housing 2, under which latching projections 51 there then engage collar sections 52 protruding radially from the indexing-mechanism housing 34.

The latching projections 51 are positioned in their vertical orientation in such a manner that the vertical displaceability of the step-by-step indexing mechanism 11 is ensured during actuation of the stroke of the cartridge 3.

The configuration selected enables the latching projections 51 to form holding-down devices which retain the step-by-step indexing mechanism 11 in the housing 2 when the cartridge 3 is pulled off.

In a further embodiment (not illustrated), a combination of the embodiments according to the illustrations in FIGS. 3 and 4 can be provided, in which the step-by-step indexing mechanism 11 is fixed by latching on the collar 41 on the cartridge-head side by means of the latching spring tongue 39. A pre-assembled cartridge/step-by-step indexing-mechanism unit of this type is introduced into the housing 2 before a first use of the hand-held device 1, with collar portions 52, which protrude radially on the indexing-mechanism housing 34, running over latching projections 51 on the device-housing side, in accordance with the second exemplary embodiment, which results in a final fixing of the step-by-step indexing mechanism 11 in the housing 2. This latching between step-by-step indexing mechanism 11 and housing 2 is selected to be stronger than the latching between step-by-step indexing mechanism 11 and cartridge 3; accordingly, a pulling-off of the cartridge 3 after being used for the first time results in the latching between cartridge 3 and step-by-step indexing mechanism 11 being undone. The reinsertion of the cartridge 3 is facilitated by a relatively weak latching-spring formation for interaction with the collar 41 on the cartridge-head side.

Both in the case of the previously described embodiment and in the case of the embodiment according to the illustration in FIG. 4, there is the possibility of releasing the latching between device housing 2 and step-by-step indexing mechanism 11 after the cartridge 3 is removed from the housing 2 itself.

The illustration in FIG. 4a shows a further embodiment building on the configuration shown in FIG. 4. For further fixing of the cartridge 3—in addition to a conventional clamping mounting of the valve tube 5 in the supporting portion 9 on the hand-held device-housing side—a blocking of the cartridge 3 in the region of the upper ring-part housing 6 is provided. Retaining fingers 55 which are directed obliquely downwards and are in one piece with the upper housing part 6 and from the same material protrude on the inner circumferential side of this upper housing ring part 6. These retaining fingers 55 are positioned in such a manner that their free peripheral edges enter in a blocking manner, in the associated position with respect to the cartridge 3, into the waist region of the cartridge 3, which region is formed behind the cartridge head 4, in order thereby to block the cartridge 3.

Furthermore, the retaining fingers 55 are formed in such a manner that they can be overrun by the cartridge head 4, at least during a first equipping of the housing 2 with the cartridge 3.

The cartridge 3 is therefore secured on the hand-held device housing 2, in particular on the upper housing part 6.

The illustration in FIG. 5 shows a further embodiment. In this, the cartridge 3 is also secured on the upper housing part 6 by means of retaining fingers 55. This upper housing part 6 can be released from the lower housing part 7, which forms the mouthpiece 8, the separation of the two housing parts 6 and 7 being undertaken approximately in the region in which the plate-shaped step-by-step indexing-mechanism housing 34 is positioned.

In the assembled position of the two housing parts 6 and 7, the latter are preferably latched, for which purpose one housing part has a latching nose and the other housing part has a correspondingly positioned latching fixture.

As a result of this separation which is made possible, an improved cleaning of the mouthpiece 8, in particular of the bending portion having the stepped portion 9, is achieved. This is furthermore facilitated by the entire step-by-step indexing mechanism 11, which is formed as a compact sub-assembly, being removable in an extremely simple manner from the lower housing part 7 and therefore being able to be brought for separate cleaning. In the exemplary embodiment illustrated, no fixing means-such as, for example, latching projections 51 which interact with collar portions 52, are provided. On the contrary, the entire step-by-step indexing mechanism 11 is fixed in the lower housing part 7 in interaction with the cartridge 3 in the position of use, with the step-by-step indexing mechanism 11 being aligned between the supporting portion 9 and the facing end surface of the cartridge head 4 (as also illustrated with reference to the embodiment shown in FIG. 4a).

Also in this embodiment, the step-by-step indexing mechanism 11 is secured against rotational displacement about the axis x-x by a positive connection between step-by-step indexing mechanism 11 and lower housing part 7.

The invention claimed is:

1. Hand-held device for apportioned delivery of sprayable substances having a cartridge which has a valve tube seated on a supporting portion and is linearly displaceable by pressing in a housing into an open position for delivery, and an indexing mechanism which is moved during an opening stroke of the cartridge for registering and displaying delivery actuations which have been carried out, which indexing mechanism is disposed in the housing centrally below an opening-side end wall of the cartridge, overlappingly with respect to the valve tube of the cartridge, and having, disposed in the housing, step-by-step indexing mechanism indexing members which revolve about axes lying in the longitudinal direction of the cartridge, characterized in that the housing, including a base and the step-by-step indexing mechanism is displaceable downward as a whole onto the supporting portion by the advance of the cartridge and the displacement movement rotates a step-by-step indexing finger star.

2. Hand-held device according to claim 1, characterized in that a graduated ring of the step-by-step indexing mechanism is rotated step-by-step by a toothed ring, via a planet-wheel gear mechanism, the planet wheel gear mechanism being mounted in a hole in the graduated ring and an associated sun wheel being seated on a disk having teeth on the lower side.

3. Hand-held device according to claim 1, characterized in that a toothed ring has at least one slot, which extends from a lower peripheral edge in a direction obliquely upwards, for entry of a step-by-step indexing finger of the step-by-step indexing-finger star.

4. Hand-held device according to claim 1, characterized in that the step-by-step indexing-mechanism housing, which is configured as a plate-like housing, has a central hole for the passage of the valve tube, which hole widens at the cartridge end for the entry of a collar which protrudes on an opening side of the cartridge and behind a region of which a resilient latching between step-by-step indexing-mechanism housing and cartridge takes place.

5. Hand-held device according to claim 1, characterized by a double latching of the step-by-step indexing-mechanism housing, which is configured as a plate-like housing, in such a manner that, in addition to the double latching to a collar of the cartridge, a second stronger latching takes place in the hand-held device housing.

6. Hand-held device according to claim 1, characterized in that a stronger latching in the hand-held device housing can itself be released after removal of the cartridge from the hand-held device housing.

7. Hand-held device according claim 1, characterized in that the cartridge is blocked against being pulled off by means of retaining fingers which are formed pointing obliquely downwards in the hand-held device housing.

* * * * *